US010354758B2

(12) United States Patent
Yang et al.

(10) Patent No.: US 10,354,758 B2
(45) Date of Patent: Jul. 16, 2019

(54) SYSTEM AND METHOD FOR PATIENT-SPECIFIC IMAGE-BASED SIMULATION OF ATRIAL ELECTROPHYSIOLOGY

(71) Applicant: Siemens Healthcare GmbH, Munich (DE)

(72) Inventors: Huanhuan Yang, Plainsboro, NJ (US); Tiziano Passerini, Plainsboro, NJ (US); Bogdan Georgescu, Plainsboro, NJ (US); Tommaso Mansi, Plainsboro, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 640 days.

(21) Appl. No.: 14/839,393

(22) Filed: Aug. 28, 2015

(65) Prior Publication Data
US 2016/0058520 A1 Mar. 3, 2016

Related U.S. Application Data

(60) Provisional application No. 62/042,977, filed on Aug. 28, 2014.

(51) Int. Cl.
*G16H 50/50* (2018.01)
*A61B 34/10* (2016.01)
*A61B 18/00* (2006.01)
*A61B 18/14* (2006.01)

(52) U.S. Cl.
CPC ............ *G16H 50/50* (2018.01); *A61B 34/10* (2016.02); *A61B 18/1492* (2013.01); *A61B 2018/00267* (2013.01); *A61B 2018/00351* (2013.01); *A61B 2018/00577* (2013.01); *A61B 2018/00839* (2013.01); *A61B 2034/104* (2016.02); *A61B 2034/105* (2016.02)

(58) Field of Classification Search
None
See application file for complete search history.

(56) References Cited

U.S. PATENT DOCUMENTS

| | | | |
|---|---|---|---|
| 7,916,919 | B2 | 3/2011 | Zheng et al. |
| 7,918,847 | B2 | 4/2011 | Damiano et al. |
| 8,267,927 | B2 | 9/2012 | Dalal et al. |
| 8,295,913 | B2 | 10/2012 | Haras |
| 8,644,576 | B2 | 2/2014 | Zheng et al. |
| 8,724,881 | B2 | 5/2014 | Zheng et al. |
| 2007/0049816 | A1 | 3/2007 | Damiano et al. |
| 2008/0300588 | A1 | 12/2008 | Groth et al. |
| 2009/0124896 | A1 | 5/2009 | Haras |
| 2009/0142740 | A1 | 6/2009 | Liang et al. |
| 2009/0221999 | A1 | 9/2009 | Shahidi |
| 2010/0040272 | A1 | 2/2010 | Zheng et al. |
| 2011/0015628 | A1 | 1/2011 | Dalal et al. |
| 2011/0251607 | A1 | 10/2011 | Kruecker et al. |
| 2013/0158577 | A1 | 6/2013 | Mahon et al. |
| 2013/0226542 | A1 | 8/2013 | Rapaka et al. |
| 2014/0022250 | A1 | 1/2014 | Mansi et al. |
| 2014/0136174 | A1 | 5/2014 | Audigier et al. |
| 2015/0242588 | A1 | 8/2015 | Audigier et al. |

OTHER PUBLICATIONS

Reinerth, G., Reumann, M., Seemann, G., Kayhan, N., Albers, J., Doessel, O., . . . & Vahl, C. F. (Jun. 2004). Three-dimensional electrophysiological and morphological computer models for individualisation of antiarrhythmic cardiac surgery. In International Congress Series (vol. 1268, pp. 813-818).*
Rapaka, et al., "LBM-EP: Lattice-boltzmann method for fast cardiac electrophysiology simulation from 3d images", In: Medical Image Computing and Computer-Assisted Intervention MICCAI, 2012, pp. 33-40, vol. 7511, Springer Berlin Heidelberg.
Peyrat et al., "A Computational Framework for the Statistical Analysis of Cardiac Diffusion Tensors: Application to a Small Database of Canine Hearts", IEEE Transactions on Medical Imaging, vol. 26, No. 11, pp. 1500-1514, 2007.
Zheng et al., "Multi-Part Modeling and Segmentation of Left Atrium in C-Arm CT for Image-Guided Atrial Fibrillation Ablation," IEEE Transactions on Medical Imaging, vol. 33, No. 2, pp. 318-331, 2014.
Mansi et al., "Data-Driven Reduction of a Cardiac Myofilament Model," Functional Imaging and Modeling of the Hearts, LNCS 7945, pp. 232-240, 2013.
Yang et al., "Data-Driven Model Reduction for Fast, High Fidelity Atrial, Electrophysiology Computations," Functional Imaging and Modeling of the Heart, LNCS 9126, pp. 466-474, 2015.
Almquist et al., "Modeling the Effect of Kv1.5 Block on the Canine Action Potential", Biophysical Journal, vol. 99, Nov. 2010, pp. 2726-2736.
Andrade et al., "The Clinical Profile and Pathophysiology of Atrial Fibrillation Relationships Among Clinical Features, Epidemiology, and Mechanisms", Circulation Research, Apr. 25, 2014, pp. 1453-1468.
Ashihara et al., "The Role of Fibroblasts in Complex Fractionated Electrograms During Persistent/Permanent Atrial Fibrillation Implications for Electrogram-Based Catheter Ablation", Circulation Research, Jan. 20, 2012, 23 pgs.

(Continued)

*Primary Examiner* — G Steven Vanni

(57) ABSTRACT

A method and system for simulating patient-specific atrial electrophysiology is disclosed. A patient-specific anatomical atria model is generated from medical image data of a patient. A patient-specific atria electrophysiology model is generated based on the patient-specific anatomical atria model and electrophysiology measurements of the patient. One or more virtual electrophysiological therapies are performed by performing atrial electrophysiology simulations using the patient-specific atria electrophysiology model. Atrial electrophysiology simulation results resulting from the one or more virtual electrophysiological therapies are displayed.

44 Claims, 4 Drawing Sheets

(56) References Cited

OTHER PUBLICATIONS

Atienza et al., "Translational Research in Atrial Fibrillation: A Quest for Mechanistically Based Diagnosis and Therapy", Circ Arrhythm Electrophysiol, Dec. 1, 2012, 17 pgs.
Burstein et al., "Changes in Connexin Expression and the Atrial Fibrillation Substrate in Congestive Heart Failure", Circulation Research, Dec. 4, 2009, pp. 1213-1222.
Camm et al., "2012 focused update of the ESC Guidelines for the management of atrial fibrillation", European Heart Journal, 2012, pp. 2719-2747.
Clayton et al., "Models of cardiac tissue electrophysiology: Progress, challenges and open questions", Progress in Biophysics and Molecular Biology, 2010, pp. 1-27.
Courtemanche et al., "Ionic mechanisms underlying human atrial action potential properties: insights from a mathematical model", The American Physiological Society, 1998, pp. H301-H321.
Dang et al., "Evaluation of Ablation Patterns Using a Biophysical Model of Atrial Fibrillation", Annals of Biomedical Engineering, vol. 33, No. 4, Apr. 2005, pp. 465-474.
Fenton et al., "Cardiac arrhythmia", Scholarpedia, 2008, 15 pgs.
Ferguson et al., "Atrial fibrillation: stroke prevention in focus", Australian Critical Care, vol. 27, Issue 2, May 2014, pp. 92-98.
Haissaguerre et al., "Spontaneous Initiation of Atrial Fibrillation by Ectopic Beats Originating in the Pulmonary Veins", The New England Journal of Medicine, 1998, vol. 339, No. 10, pp. 659-666.
Zheng et al., "Marginal Space Learning for Efficient Detection of 2D/3D Anatomical Structures in Medical Images", Proc. International Processing in Medical Imaging, 2009, 12 pgs.
Krummen et al, "Mechanisms for Human Atrial Fibrillation Initiation: Clinical and Computational Studies of Repolarization Restitution and Activation Latency", Circ Arrhythm Electrophysiol, Dec. 2012, 20 pgs.
Krueger et al., "Personalization of Atrial Anatomy and Electrophysiology as a Basis for Clinical Modeling of Radio-Frequency Ablation of Atrial Fibrillation", IEEE Transactions on Medical Imaging, vol. 32, Issue 1, Jan. 2013.
Labarthe, et al., "A Computational Bilayer Surface Model of Human Atria", FIMH 2013, 7th International Conference on Fonctional Imaging and Modeling of the Heart, Jun. 2013, London, United Kingdom, Springer, 12 pgs.
Nygren et al., "Mathematical Model of an Adult Human Atrial Cell: The Role of K+ Currents in Repolarization", Circulation Research, 1998, 20 pgs.
Pappone et al., "Robotic Magnetic Navigation for Atrial Fibrillation Ablation", Journal of the American College of Cardiology, vol. 47, No. 7, 2006, pp. 1391-1400.
Tan et al., "Left Atrial Wall Thickness: Anatomic Aspects Relevant to Catheter Ablation of Atrial Fibrillation", Chinese Medical Journal, Jan. 2012.
Tobon et al., "A Three-Dimensional Human Atrial Model with Fiber Orientation. Electrograms and Arrhythmic Activiation Patterns Relationship", PLOS One, Feb. 2013, vol. 8, Issue 2, 13 pgs.
Voigt et al., "Cellular and Molecular Mechanisms of Atrial Arrhythmogenesis in Patients with Paroxysmal Atrial Fibrillation", Circulation Research, 2014, 46 pgs.

\* cited by examiner (a)　　　(b)　　　(c)

Cardiac electrophysiology　　Torso potential　　ECG signal
302　　　　　　　　　304　　　　　　　306 t = 1.57sec   t = 1.61sec   t = 1.65sec   t = 1.69sec t = 0.76sec   t = 0.79sec

SYSTEM AND METHOD FOR PATIENT-SPECIFIC IMAGE-BASED SIMULATION OF ATRIAL ELECTROPHYSIOLOGY

This application claims the benefit of U.S. Provisional Application No. 62/042,977, filed Aug. 28, 2014, the disclosure of which is herein incorporated by reference in its entirety.

BACKGROUND OF THE INVENTION

The present invention relates to medical image-based simulation of atrial electrophysiology, and more particularly to medical image-based simulation of atrial electrophysiology using a personalized computational model of atrial electrophysiology.

Cardiac arrhythmia is any of a group of conditions in which the rate or rhythm of the heartbeat is irregular. Cardiac arrhythmia is typically associated with abnormal initiation and/or abnormal propagation of a wave of cardiac excitation. The most common atrial arrhythmias are atrial flutter and atrial fibrillation. Atrial flutter (AFL) is a reentrant supraventricular arrhythmia characterized by a rapid "sawtooth" appearance of the electrocardiogram (ECG) owing to the presence of multiple P waves between the QRS complexes. AFL can be paroxysmal (which lasts for hours or days) or persistent (which is more or less permanent) and often induces electrical remodeling and thereby can serve as a precursor to atrial fibrillation.

Atrial fibrillation (AFib) is the most common cardiac arrhythmia. As one of the major risk factors for worsening heart failure (HF), AFib is associated with significant morbidity and mortality. AFib is characterized by rapid, seemingly chaotic atrial activation, and is clinically confirmed with the absence of P waves and irregular ventricular rate (QRSs) in the ECG. AFib can be paroxysmal or persistent. Multiple pathophysiological processes have been identified as contributors to the initiation and maintenance of AFib; however, many aspects remain incompletely understood.

Treatment options for atrial arrhythmia include direct electrical cardioversion, pharmacologic therapy, and catheter ablation of the underlying reentrant circuit. No current antiarrhythmic drug (AAD) is atrial specific and therefore care must be taken to avoid adverse effects on the ventricular rhythm. The seemingly superior ablation approach still has unknown effects in terms of mortality, and the most effective but less invasive ablation line pattern is still under study. Tools that provide better patient stratification and therapy planning for atrial arrhythmias are desirable.

BRIEF SUMMARY OF THE INVENTION

The present invention provides a method and system for image-based patient-specific simulation of atrial electrophysiology. Embodiments of the present invention can be used for optimal planning of ablative and/or drug therapies for atrial arrhythmias. Embodiments of the present invention can also be performed in real time or near real time to provide model-based guidance during an intervention procedure.

In one embodiment of the present invention, a patient-specific anatomical atria model is generated from medical image data of a patient. A patient-specific atria electrophysiology model is generated based on the patient-specific anatomical atria model and electrophysiology measurements of the patient. One or more virtual electrophysiological therapies are performed by performing atrial electrophysiology simulations using the patient-specific atria electrophysiology model. Atrial electrophysiology simulation results resulting from the one or more virtual electrophysiological therapies are displayed.

These and other advantages of the invention will be apparent to those of ordinary skill in the art by reference to the following detailed description and the accompanying drawings.

DETAILED DESCRIPTION

The present invention relates to image-based patient-specific simulation of atrial electrophysiology. Embodiments of the present invention are described herein to give a visual understanding of the methods for patient-specific simulation of atrial electrophysiology using medical imaging data. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Progress of electrophysiological (EP) experiments in cells, tissue, and human patients have led to a rapid increase in the body knowledge regarding the mechanisms underlying atrial arrhythmia. Modeling and simulation of atrial electrophysiology and arrhythmias can play an important role in assisting the clinical treatment of atrial arrhythmia and in contributing to patient-specific optimization of cardiac care. Computational EP models are typically calculated using the finite element method. However, such an approach can be easily adapted to highly parallel architectures and does not scale up, leading to long computation times. Existing methods for EP computation suffer from limitations that hinder their use in clinical applications including high computational demand from the EP solver (e.g., finite element method) and lack of good model personalization strategy.

Embodiments of the present invention provide a fast personalized computational model of atrial electrophysiology based on patient-specific medical images. Embodiments of the present invention can be performed off-line as a planning tool or can be performed in real-time or near real-time to provide model-based guidance during an intervention procedure. As such, embodiments of the present invention can be viewed as a "GPS" system for ablation therapy of atrial arrhythmias.

Figure 1:
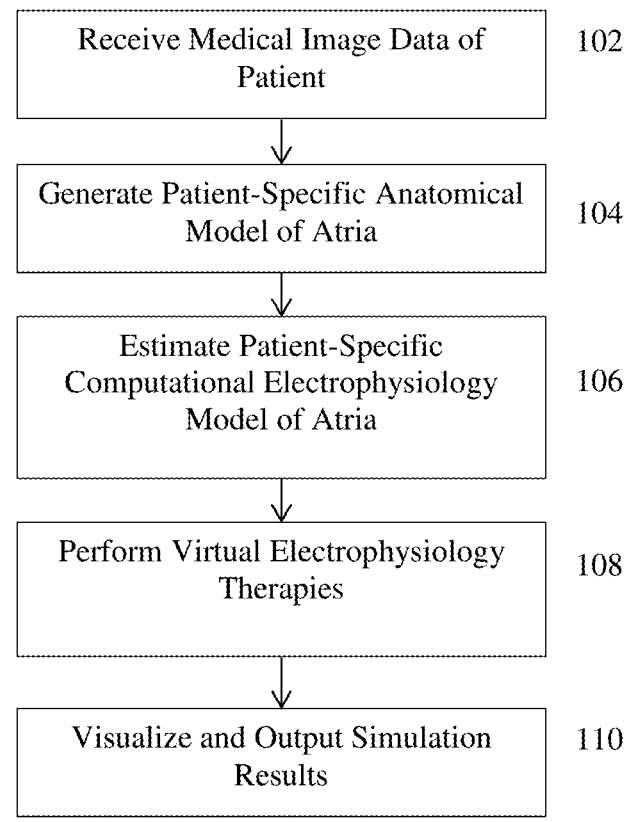
FIG. 1 illustrates a method for patient-specific simulation of atrial electrophysiology according to an embodiment of the present invention.

FIG. 1 illustrates a method for patient-specific simulation of atrial electrophysiology according to an embodiment of the present invention. The method of FIG. 1 can be performed in real-time or near real-time during an electrophysiology intervention, such as an ablation procedure to correct an atrial arrhythmia. Alternatively, the method of FIG. 1 may be performed offline in advance of an electrophysiological intervention or drug therapy in order to plan the electrophysiological intervention or drug therapy.

At step 102, medical image data of the patient is received. The medical image data can be acquired using any type of medical imaging modality, such as magnetic resonance imaging (MRI), computed tomography (CT), three-dimensional rotational angiography, ultrasound (US), etc., provided that the heart is visible in the medical image data. In an advantageous implementation, the medical image data includes three dimensional (3D) and/or 4D (3D+time) medical image data. The medical image data can be received directly from an image acquisition device, such as an MRI scanner, a CT scanner, a C-arm image-acquisition device, or an US scanner, or the medical image data can be received by loading previously stored medical image data of the patient. In an advantageous embodiment, the medical image data can include 3D or 4D interventional (intraoperative) images (e.g., cine MRI or delayed enhanced MRI (DE-MRI)) that are acquired at the beginning of the electrophysiological intervention and received in real-time or near real-time from the medical image acquisition device. However, it is also possible that the medical image data can be pre-operative cardiac image data acquired prior to an electrophysiological intervention.

At step 104, a patient-specific anatomical model of the patient's atria is generated from the medical image data of the patient. The patient-specific anatomical model of the atria can be a bi-atrial model of both the left and right atria or an individual model of either the left or right atrium. In another possible implementation, a full four-chamber heart model may be generated. The atria are segmented from the medical image data of the patient and a detailed patient-specific anatomical model of the atria is generated including important anatomical structures for conduction of atrial excitation, such as the SA node, the Bachmann's bundle (BB), and other heterogeneous structures like the *crista terminalis*, pectinate muscles (PM), and appendages (APG). In an advantageous embodiment, the atria, including these anatomical structures, can be segmented in the medical image data using a multi-part atrial model.

Figure 2:
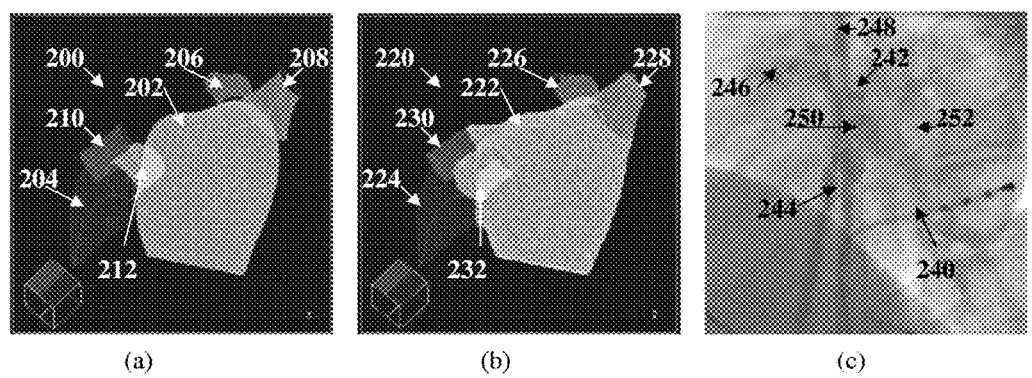
FIG. 2 illustrates a part-based left atrium (LA) model according to an embodiment of the present invention.

FIG. 2 illustrates a part-based left atrium (LA) model according to an embodiment of the present invention. As shown in image (a) of FIG. 2, the part-based LA model 200 includes the LA chamber body 202, appendage 204, and four major pulmonary veins (PVs) 206, 208, 210, and 212. The four major PVs are the left inferior PV 212, the left superior PV 210, the right inferior PV 208, and the right superior PV 206. The shape of the appendage 204 is close to a tilted cone and the PVs 206, 208, 210, and 212 each have a tubular structure. Each LA part 202, 204, 206, 208, 210, and 212 is a much simpler anatomical structure as compared to a holistic LA structure, and therefore can be detected and segmented using a model based approach. According to an advantageous embodiment, the LA chamber body 202 and appendage 204 can be segmented first together using a Marginal Space Learning (MSL) framework. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. Each classifier can be a probabilistic boosting tree (PBT) classifier trained based on annotated training data. The classifiers in the lower dimensional marginal spaces are used to prune the searching space efficiently. This object localization stage results in an estimated transformation (position, orientation, and scale) of the object (e.g., heart chamber). After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference. Once the LA chamber body 202 and appendage 204 are segmented, the remaining LA parts 206, 208, 210, and 212 are segmented using MSL-based segmentation subject to a statistical shape constraint based on the segmented LA chamber body 202.

Once the LA parts are segmented in the medical image data, they are combined into a consolidated mesh model. Image (b) of FIG. 2 shows a consolidated LA mesh 220 including the LA chamber 222, appendage 224, and PVs 226, 228, 230, and 232. Image (c) of FIG. 2 shows the overlay of a consolidated LA mesh 240 including the LA chamber 242, appendage 244, and PVs 246, 248, 250, and 252 on a 2D fluoroscopic image. Additional details regarding methods for part-based atrial segmentation are described in U.S. Pat. Nos. 8,644,576 and 8,724,881, which are incorporated herein by reference in their entirety. The right atrium (RA) can be segmented similarly either holistically or using a part-based method using MSL-based segmented. In a possible implementation, the LA and RA models can be combined into a bi-atrial mesh. Atrial anatomical structures, such as the SA node, Bachmann's bundle (BB), *crista terminalis*, and pectinate muscles (PM), can be tagged on the mesh vertices of the atrial mesh.

The fiber orientation can be modeled based on historical observations. In a possible implementation, it can be assumed that the atrial tissue is isotropic and propagation is equally likely in all directions. Alternatively, if in-vivo diffusion tensor (DT) MR images are available, DT MR images of the patient's cardiac fibers can be directly mapped to the anatomical model through image registration. In this case, the DT MR image is non-linearly registered to the medical image in which the LA and RA models are detected. The resulting transformation is used to deform the tensor field in the DT MR image towards the anatomical model. The Finite Strain method, the details of which are described in Peyrat et al., "A Computational Framework for the Statistical Analysis of Cardiac Diffusion Tensors: Application to a Small Database of Canine Hearts", *IEEE TMI*, 26(11):1500-1514, 2007, which is incorporated herein by reference, is used to reorient the tensors once the tensors are registered to the anatomical model. It is also possible, that an atlas of fiber architecture is available and the atlas is registered to the patient-specific anatomical model using standard image registration techniques.

The success rate of pulmonary vein isolation (PVI) in AFib ablation therapy depends on knowledge of local atrial wall thickness, which is non-uniform with values ranging between 0.8 mm and 3 mm. Regional atrial wall thickness can be extracted from high resolution MRI images, but it can be time-consuming the extract the atrial wall thickness for the whole atrium. An alternative way to generate the atrial model with non-uniform wall thickness is to perform mesh thickening (for non-ablation areas) using level-set thresholding from the patient's atria images.

If tissue fibrosis (e.g., scar tissue) can be identified in the medical images, this information is also included in the patient-specific anatomical model. For example, scar tissue and border zone tissue can be segmented using DE-MRI image data. The 3D anatomical model of the atria can be rigidly registered on a DE-MRI image using the coordinates of the MR scanner plus correlations between image information in the DE-MRI image and the 3D anatomical model. An expectation-minimization algorithm with belief prior and spatial regularization can then be employed to segment the scar and border zone tissue. This method works on in-vivo, multi-modality images and adds smoothing constraints for increased robustness to noise. Healthy tissue and scar tissue are modeled using a Gaussian mixture model with two modes. Given a three-class segmentation, the parameters of the mixture model are estimated, from which a belief value A is derived. Voxels with A<0.5 are rejected from the model and classified as border zone. The border zone is a zone surrounding the scar tissue that represents healing tissue. For increased robustness and regularity, Markov random fields are employed to reject voxels according to the state of neighboring voxels. Furthermore, voxels farther than N-mm from the current scar estimate are never rejected, assuming that border zone can only be found in the proximity of scars. A graph-cut algorithm is also employed to estimate smooth interfaces between tissue types. The graph-cut algorithm is initialized with a coarse classification obtained using a k-means algorithm or similar algorithm and is iterated until convergence (e.g., when the parameters of the mixture model do not change anymore). The segmented scar tissue and surrounding border zone is then mapped to the volumetric mesh representation of the atria.

Returning to FIG. 1, at step 106, a patient-specific computational electrophysiology (EP) model of the atria is estimated based on the patient-specific anatomical model and measured EP data of the patient. The patient-specific computational EP model is a computational model of atrial electrophysiology, which is personalized by estimating patient-specific parameters of the computational EP model representing tissue properties of the atrial tissue based on the measured EP data of the patient. The patient-specific computational EP model of the atria computes atrial electrophysiology and, once personalized, can be used to perform virtual electrophysiological interventions, for example to guide an electrophysiologist towards an optimal pacing site and identify an optimal ablation target. To that end, in an advantageous implementation, the computational EP model is fast enough to be personalized and executed on-line during the clinical intervention, while also being accurate enough to capture the complex pathological patterns observed in atrial arrhythmias.

Computational EP models are typically calculated using finite element methods. However, finite element methods cannot be easily adapted to highly parallel architectures and do not scale well. According to an advantageous implementation, embodiments of the present invention utilize a Lattice-Boltzmann method for electrophysiology (LBM-EP) to solve a monodomain tissue model over the patient-specific atria geometry, using a multi-cellular model. In this method, a Cartesian grid domain for electrophysiology computations is calculated using the patient-specific anatomical model of the atria. A Cartesian grid, with uniform grid spacing or possibly with unequal and spatially varying spacing, is first generated in a bounding box surrounding the anatomical model of the atria. Grid spacing can be defined by the user or fixed in the system. A level-set representation is then calculated from the patient-specific anatomical model as follows. For every node x of the grid, the shortest distance to the anatomical model mesh is calculated, and assigned to that node. In an advantageous embodiment, nodes inside the myocardium are defined by positive distances, and nodes not inside the myocardium are defined by negative distances. The opposite convention can be utilized as well without any modification. Nodes at myocardium, endocardia, and epicardium are tagged as such, as well as other nodes pertaining to the atrial anatomical structures important to the conduction of atrial excitation. For example, the nodes of the patient-specific anatomical model on the Cartesian grid corresponding to the SA, BB, crista terminalis, pectinate muscles, and appendages can be tagged. Available scars and border zones are also reported in the domain through additional level-set information and the conductivity for such regions can be set to a predetermined reduced value or to zero. Fiber orientation f(x) is mapped to each node using rasterization techniques or is recomputed from the mapped endocardial and epicardial zones directly. Cell model parameters, such as the ionic current conductance c(x), are assigned to each node x.

The computational EP model of the atria calculates the transmembrane potential at each node within the atria using the Lattice-Boltzmann Method for Electrophysiology (LBM-EP). The computational EP model calculates the variation of the transmembrane potential v(x,t) over time according to the mono-domain equation:

$$\frac{dv(x,t)}{dt} = R(x,t) + \nabla \cdot c(x)D(x)\nabla v(x,t), \quad (1)$$

where R(x,t) is a reaction term describing the cellular mechanisms giving rise to the action potential, c(x) is the local ionic current conductance, D(x) is the anisotropy (transverse isotropy) matrix defined by $(1-\rho)f(x)f(x)^T+\rho Id$, $\rho$ being the ratio between the cross-fiber diffusivity and the fiber diffusivity (typically $\rho$=0.11-0.25). It is also possible to use fully isotropic tensors D(x) for improved characterization of the atrial fiber architecture.

The choice of the reaction term R(x,t) depends on the cellular model of cardiac electrophysiology that is used. According to an advantageous embodiment of the present invention, a multi-cell EP model can be used to model the EP of the atria. In order to describe the effect of non-homogeneity of the tissue on the atrial EP, the Cartesian nodes in the computational domain of the LBM-EP solver pertaining to the various atrial anatomical structures can be tagged and assigned with different cellular models and/or electrical conductivity values. In an exemplary implementation, the Courtemanche-Ramirez-Nattel (CRN) human atrial cell model, described in Courtemanche et al., "Ionic Mechanisms Underlying Human Atrial Action Potential Properties: Insights from a Mathematical Model", *Am. J. Physiol.* 275, H301-H321 (1998), can be used as the atrial cell mode. The CRN atrial cell model features 35 static parameters and 21 ordinary differential equations to describe 12 ionic channels, the corresponding gating variables and ionic concentrations.

Equation (1) is solved using the Lattice-Boltzmann method for electrophysiology, referred to herein as LBM-EP. LBM-EP is a highly parallelizable algorithm to solve monodomain electrophysiology equations. The LBM-EP algorithm is described in greater detail in United States Published Patent Application No. 2013/0226542, entitled "Method and System for Fast Patient-Specific Cardiac Electrophysiology Simulations for Therapy Planning and Guidance", which is incorporated herein by reference in its entirety. Contrary to standard finite-element methods, LBM-EP does not explicitly solve the reaction-diffusion equation but rather computes the "movement" of particles on a Cartesian grid, from which the reaction-diffusion behavior emerges. The particles can move according to fixed directions (or connectivities), with a certain probability. The algorithm includes two node-wise steps: streaming, which makes the particle jump from one node to another; and collision, which takes care of mass preservation and boundary conditions. It can be mathematically shown that this simple algorithm reproduces dynamics of the reaction-diffusion equation. In order to compute the cardiac electrophysiology using LBM-EP, domain boundaries are represented as level-sets and tissue anisotropy is modeled. In sinus rhythm, the electrocardiography model can be computed with periodic stimulus at the septum to mimic the fast conducting His bundle.

Since the LBM-EP method is completely node-wise and the time-integration is explicit, the computations can be done locally and the method is therefore easily adapted to highly parallel architectures. In an advantageous embodiment, the method can be implemented on one or more general purpose graphics processing units (GPGPU), which enables near real-time and accurate cardiac electrophysiology computation during the intervention. In this embodiment, this method can be optimized to fully benefit from the computational power of GPGPUs. For example, adaptive computational block aggregation can be performed to balance between computational power and memory bandwidth. Adaptive time-stepping methods can also be implemented to take into account the current EP dynamics, in particular in sinus rhythm regions. For example, small time steps can be used when the fast front propagation is occurring, larger time steps can be used during the refractory period, and even larger time steps can be used during the depolarization state. Adaptive mesh refinement techniques can also be implemented to reduce the overall computational effort in the presence of thick-walled structures (e.g., ventricles) and thin-walled structures (e.g., atria). The model can be interfaced with model repositories for greater flexibility.

The computational EP model of the atria is coupled with a boundary element model of potential propagation in soft tissue in order to calculate an ECG resulting from the simulated cardiac electrophysiology. This allows body surface ECG measurements of the patient to be back-mapped to the atrial model for personalization of the computation EP model. The computational EP model of the atria computes a transmembrane potential for each node of the patient-specific anatomical model on the computational domain at each time step. An extra-cellular potential $\phi_e$ is calculated at each node of the computational domain based on the transmembrane potential v(x,t) using a closed-form expression ($\Omega$ defines the computational domain; $|\Omega|$ is the number of elements therein):

$$\phi_e(x, t) = \frac{\lambda}{1+\lambda} \frac{1}{|\Omega|} \int_\Omega [v(y, t) - v(x, t)] dy, \quad (2)$$

where $\lambda$ is a constant diffusion anisotropy ratio, $\lambda = D_i(x)/D_e(x)$, and $D_i$ and $D_e$ are intra- and extra-cellular diffusivity tensors, respectively. The extra-cellular potential $\phi_e$ is then mapped back to the atria surface mesh using tri-linear interpolation. The extra-cellular potentials are then projected onto a torso surface mesh using a boundary element method (BEM). The potential $\phi(x)$ at any point x of the thoracic domain (torso surface mesh) can be calculated as:

$$\phi(x) = \frac{1}{4\pi} \int_{S_B} \phi_b \frac{r \cdot n}{\|r\|^3} dS_B - \frac{1}{4\pi} \int_{S_H} \left[ \phi_e \frac{r \cdot n}{\|r\|^3} + \frac{\nabla \phi_e \cdot n}{\|r\|} \right] dS_H, \quad (3)$$

where r is the vector defined by x and the integration point n, while $S_B$ and $S_H$ are the torso and epicardium surfaces, respectively. The body surface potential at the torso, $\phi_b$, can be expressed as a function of the extra-cellular potential $\phi_e$, which allows the potential to be calculated at any point on the torso. The torso mesh can be segmented from the medical image data using machine learning algorithms. According to a possible implementation, the body surface potential $\phi_b$ can be calculated for each vertex on the torso mesh. In another possible implementation, the body surface potential $\phi_b$ may be calculated only for vertices on the torso mesh corresponding to the locations of leads used to acquire the measured ECG signals (e.g., 12 lead ECG) of the patient. A simulated ECG signal is calculated using the body surface potentials calculated at the ECG lead positions, and ECG features, such as the duration of the QRS complex $\Delta_{QRS}$ and the electrical axis angle $\alpha_{EA}$ can be derived automatically from the simulated ECG signal. It should be noted that in the above description a homogeneous torso model is employed. However, this can be extended to a heterogeneous torso model that incorporates muscle, lungs, bones, fat and other tissues, as identified in medical images. Each tissue would then have different electrical conductivity.

Figure 3:
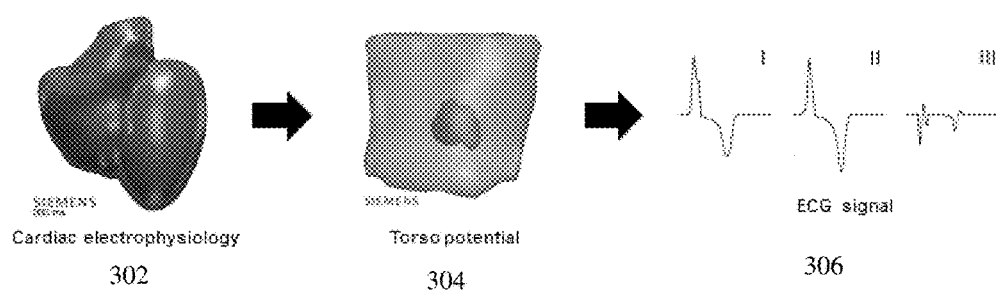
FIG. 3 illustrates exemplary results for simulating cardiac electrophysiology using a computational electrophysiology (EP) model.

FIG. 3 illustrates exemplary results for simulating cardiac electrophysiology using the computational EP model. As shown in FIG. 3, image 302 shows a map of transmembrane potentials resulting from simulating cardiac EP using the computational EP model, image 304 shows a map of torso potentials generated from the simulated cardiac transmembrane potentials, and image 306 shows an ECG signal generated based on torso potentials at ECG lead locations.

The computational EP model of the atria needs to be personalized in order to be predictive for a specific patient. The computational EP model of the atria is personalized based on EP measurements of the patient, such as invasive cardiac EP maps or body surface potential maps. In an exemplary embodiment, the electrophysiology (EP) data of the patient is first fused with the patient-specific anatomical model of the atria. The EP data of the patient can include invasive cardiac EP maps acquired for the patient and/or body surface potential measurements. Body surface potential measurements are measurements of electrical potentials on the torso of the patient and can refer to body surface potential maps acquired using body surface mapping (BSM) or ECG measurements of the patient using ECG leads on a patient's torso (e.g., 12 lead ECG measurements). Invasive cardiac maps are generated invasively by measuring potentials at various points in the heart over time, for example using a catheter mapping system or a catheter basket system. In order to personalize a computational EP model using invasive cardiac EP maps, the cardiac EP data is registered to the patient-specific anatomical model of the atria.

In order to fuse body surface potential measurements (e.g., body surface potential maps acquired using BSM or ECG measurements) to the patient-specific anatomical model of the atria, the body surface measurements are mapped to a patient-specific torso model that is registered to the patient-specific anatomical model of the atria. A 3D image of the patient's torso can be acquired, for example at the beginning of the intervention, and a triangulated mesh of the patient's torso can be segmented from the 3D image using a segmentation algorithm, such as graph cuts. In a case in which 3D torso images cannot be acquired, 2D MRI scout images can used to generate a torso model. In this case, contours of the visible torso in the 2D scout images can be automatically extracted, for example using graph-cuts. A stored 3D torso atlas can then be registered based on the 2D scout images using an affine transformation to match the torso contours extracted from the 2D scout images. This registration algorithm leverages the scout image positions (axial, sagittal and coronal) for increased robustness and minimizes risks of local minima. Once the torso is modeled, the patient-specific torso model can be automatically registered to the heart model using the scanner coordinates. Lead positions from which the body surface potentials were measured are mapped to the torso model. For example the lead positions can be mapped automatically or using user-defined landmarks. The body surface potential measurements can then be back-projected to the patient-specific anatomical model of the torso.

Once the patient-specific torso model is registered to the patient-specific anatomical model of the atria, an electrical model of diffusion in the torso can be used to describe the coupling relationship between the heart and the torso. As described above, electrical potentials on the torso can be calculated from cardiac potentials by first inferring extra-cellular potentials from transmembrane potentials on the atrium, and then solving a Poisson equation using the boundary element method (BEM). The electrical coupling between the heart mesh and the torso mesh can be modeled by the linear relationship $\forall t, Y_t = T^* X_t$, where $X_t(x)$ denotes the extra-cellular potentials on the epicardium, $Y_t(x)$ denotes the torso potentials, and T is the coupling matrix obtained by boundary element discretization of the heart-torso geometry and solving the Poisson equation for electrical potentials.

The EP measurements of the patient are used to personalize the electrical conductivity values and multi-cell model parameters at the nodes of the computational domain. For a detailed multi-cell model specific for the atria, such as the CRN atrial cell model which has 35 parameters, a model reduction approach can be used to reduce the computational cost and number of model parameters. For example, a reduced model can be constructed by action potential (AP) manifold learning to reduce the number model parameters followed by learning a regression model to predict the parameters in the reduce AP manifold. This speeds up the personalization procedure, because the more parameters to be estimated, the larger number of iterations needed for the forward solver.

In one embodiment, the personalization of the computational EP model can be performed using an inverse problem approach based on a comparison of simulated EP data generated by performing simulations using the computational EP model and the EP measurements of the patient. In particular, the personalization can be formulated as an optimization problem with the goal of minimizing the point-wise difference between the calculated (simulated) activation times using the computational EP model and the activation times in the measured EP data of the patient over all the nodes of the computational domain (i.e., over all the nodes of the patient-specific anatomical model of the atria). For increased estimation convergence and robustness to local minima, a coarse-to-fine strategy can be employed. In the coarse-to-fine strategy, a parameter value (e.g., electrical conductivity c) is first estimated for both atria. Areas with larger errors are then partitioned, and one parameter value per partition is estimated, initialized to the value of the previous step. The procedure is then iterated until convergence.

In another embodiment, machine learning methods can be utilized to estimate personalized parameters of the computational EP model of the atria based on the EP measurements of the patient. In an offline training stage, a large database of activation maps or other EP measurements are created using the computational EP model with different parameter values. Advanced non-linear manifold learning techniques are utilized to train a regression function, and the personalized parameters are estimated on-line by applying the trained regression function to regress the local values of electrical conductivities and multi-cell model parameters given the local activation maps of the measured EP data of the patient.

According to an advantageous implementation, the personalized parameters of the patient-specific cardiac EP model can be updated online during an intervention from newly acquired EP maps, as more data is acquired. When new EP measurements are acquired and mapped to the anatomical model, they are given as input to the personalization procedure. Similarly, segmented lesions (necrosis regions resulting from ablation) can be used to update the patient-specific anatomical model of tissue substrate. In the case of the inverse problem approach, the optimizer is then run again starting from the current estimates of the electrical conductivities and multi-cell model parameters. Areas with large errors are identified and partitioned through thresholding and the optimizer is run again as described above. In the case of the machine learning approach, the trained regression function is applied again with the updated EP measurements of the patient.

In another possible embodiment, the electrical conductivity values and the cell model parameters of the multi-cell model can be assigned using a rule-based approach based on a clinical report specifying a healthy or disease state of the atrial tissue at the various locations in the atria.

Returning to FIG. 1, at step 108, virtual EP therapies are performed using the patient-specific computational EP model of the atria. The patient-specific computational EP model of the atria simulates EP (action potential propagation) in the atria. It is to be understood that in addition to simulating atrial EP and outputting visualizations of the simulated EP in response to virtual EP therapies, the patient-specific computational EP model can also perform a simulation of the patient-specific atrial EP without any therapy and output visualizations of the simulated EP. The fast patient-specific atrial EP model described herein provides a useful tool for investigating and treating the complex phenomena involved in atrial arrhythmias by simulating experimental and clinical situations that are difficult to realize in vitro or in vivo. In order to perform a virtual EP therapy, the patient-specific EP model is adjusted to reflect a particular EP therapy, and then the adjusted patient-specific EP model is used to simulate the atrial EP in response to that EP therapy.

The patient-specific computational EP model can be used to study mechanisms underlying atrial arrhythmia, since the onset and maintenance of atrial arrhythmia are still incompletely understood. A comprehensive understanding of atrial arrhythmia pathophysiology can help foster the development of pharmacological and non-pharmacological treatments and improve clinical management. Compared with in vitro experiments, the patient-specific EP model has the advantage of cost effectiveness for cellular and molecular level analyses, such as the role of $Ca^{2+}$-handling abnormalities in focal ectopic arrhythmias. Moreover, atrial EP simulations using the patient-specific computational EP model enables the study of whole-organ response which is impossible to realize in vitro. For example, the particular role of structural remodeling and fibrosis on AFib initiation and the relationship between mechanisms of AFib initiation and rate-dependent changes (restitution) in action potential duration (APD) and activation latency can be studied using patient-specific simulations performed using the patient-specific computational EP model of the atria.

In one embodiment of the present invention, the virtual EP therapies can be EP interventions, such as ablation therapy. In an advantageous implementation, the patient-specific computational EP model of the atria can provide real time or near real time model based guidance of an ablation procedure. The user (e.g., clinician) can interactively select ablation locations and ablation protocols to virtually ablate areas of the atria. Alternatively, virtual ablations can be automatically performed for various ablation locations and ablation protocols. For each virtual ablation (ablation location and ablation protocol), the patient-specific computational EP model of the atria is adjusted to reflect that ablation location and ablation protocol, and the atrial EP is simulated using the adjusted patient-specific computational EP model. In a possible implementation, the ablated area resulting from a virtual ablation is automatically given scar parameters (small/no conductivity). In another possible implementation, a model of ablation therapy is utilized to simulate the effects of heat transfer and cellular necrosis. The model of ablation therapy can be implemented as described in International Publication No. WO 2014/133924 A1, entitled "System and Method for Interactive Patient-Specific Simulation of Radiofrequency Ablation Therapy," or U.S. patent application Ser. No. 14/622,022, filed Feb. 13, 2015, entitled "System and Method for Personalized Computation of Tissue Ablation Extent Based on Medical Images," which are incorporated herein by reference in their entirety. In both cases, the computation is performed interactively, and the EP simulation using the patient-specific EP model is recalculated on the new tissue model, yielding predictors of therapy outcome. For each of the virtual ablations, simulation results can be output. For example, atrial EP maps (e.g., transmembrane potential maps, activation time maps, depolarization time maps, repolarization time maps, etc.) can be visualized and displayed on a display device. In addition, torso potentials and a simulated ECG signal can be computed from the simulated transmembrane potentials. The simulated ECG signal can be displayed on a display device and a map of the torso potentials can be visualized and displayed on the display device.

A probability of success can be calculated for each virtual ablation based on the predicted outcome. A best ablation location or ablation pattern including multiple sequential ablation locations can be automatically determined based on the virtual ablations and the best ablation location can be provided to the user, for example, by displaying a map highlighting a best ablation location or a color map showing probabilities of success of various possible ablation locations. In addition map can be displayed showing an optimal ablation pattern for interventional guidance. The target (best) ablation location and ablation protocol can be determined based on the virtual ablations by finding an ablation location and protocol that causes a minimal ablation region but still successfully treats the patient's atrial arrhythmia. In a possible implementation, the ECG signals resulting from atrial EP simulation after each virtual ablation can be displayed and user can determine which ablation therapies are successful from the ECG signals.

When the virtual ablations are used for real time or near real time guidance of an ablation procedure, the clinician can then perform the actual ablation based on the target ablation and ablation procedure. The actual outcome (e.g. ECG measurements) and produced lesion area resulting from the actual ablation can be observed and the patient-specific anatomical model of the atria and/or the patient-specific computational EP model of the atria can be adjusted to reflect the actual results of the ablation in order to improve the predictive capability of the computational EP model.

In another embodiment of the present invention, the virtual EP therapies can be pharmacological (drug) therapies for treating arrhythmia. In this case, the parameters of the multi-cell model of the patient-specific EP model can be adjusted to reflect an effect of a particular drug, and the atrial EP can then be simulated with the adjusted patient-specific EP model to simulate the drug treatment. Currently, no antiarrhythmic drug in clinic use is atrial specific or targeting a specific ion channel related to atrial arrhythmia imitation or maintenance. According to an advantageous implementation, the patient-specific EP model can be adjusted by modifying the cell model corresponding to particular ionic channels to simulated drug effects of drugs targeting those ionic channels. For example, the effects of Ikur and IkACh channel blockers, L-type Ca channel blockers, and blockers targeting the gap junction can be simulated by modifying a cellular permeability parameter in the cell model corresponding to the particular channel or channels blocked by a drug. The effect of drugs aimed at preventing or reversing fibrosis can be simulated by modifying the electrical conductivity values of fibrosis regions in the patient-specific EP model.

At step 110, atrial EP simulation results resulting from the virtual EP therapies are visualized and output. For each of the patient-specific atrial EP simulations, EP maps (e.g., transmembrane potential maps, activation time maps, depolarization time maps, repolarization time maps, etc.) can be visualized and displayed on a display device. For example, the EP maps can be overlaid on the patient-specific anatomical model of the atria and/or the medical image data of the patient and displayed on the display device. In addition, torso potentials and a simulated ECG signal can be computed from the simulated transmembrane potentials for each patient-specific atrial EP simulation. The simulated ECG signal can be displayed on a display device and a map of the torso potentials can be visualized and displayed on the display device. Maps of electrical conductivity and model parameters of the multi-cell model can be displayed as well. When the virtual therapies include virtual ablations, maps of target ablation locations and ablation protocols can be displayed as well. The ablation target locations can be highlighted on the visualization of the patient-specific anatomical model of the atria or visualized a color map indicating grades or probabilities for various ablation target locations that is overlaid on the visualization of the patient-specific anatomical heart model. In another possible implementation, the ablation targets can be output by displaying the ablation targets on an interventional image, such as an interventional MRI image, acquired during the EP intervention. For example, locations of pacing targets or ablation targets can be highlighted on the interventional image or a color map indicating grades for various pacing target locations or ablation target locations can be overlaid on the interventional image. The interventional image can then be used to guide the EP intervention.

Figure 4:
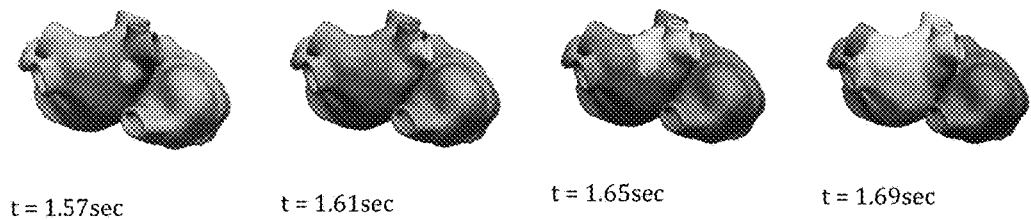
FIGS. 4 and 5 illustrate exemplary simulated action potential propagation in the atria using a patient-specific computational EP model of the atria.
Figure 5:
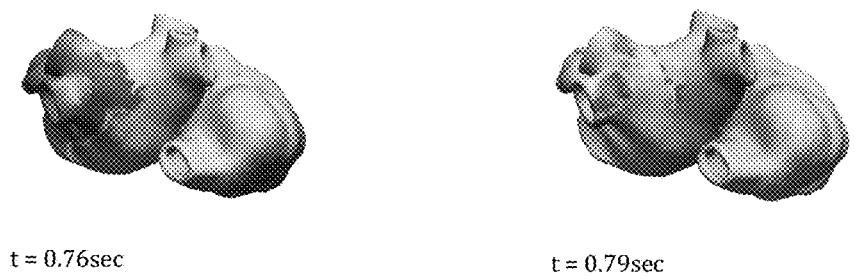

FIGS. 4 and 5 illustrate exemplary simulated action potential propagation in the atria using a patient-specific computational EP model of the atria. In FIG. 4, the simulated action potential propagation in the atria show a rotor created by ectopic firing from the right inferior pulmonary vein (RLPV). In FIG. 5, the simulated action potential propagation in the atria show AFib created by ectopic firing near pulmonary veins and tissue fibrosis.

Although bi-atrial single atrium anatomical models are described above, embodiments of the present invention can also be implemented by modeling the whole heart including all four chambers. A whole heart EP model can then be implemented using an atrioventricular (AV) node cell model. For example, this may allow for more precise modeling of junctional arrhythmias, such as AV reciprocating tachycardia, AV nodal reentrant tachycardia, junctional rhythm, and junctional tachycardia.

Figure 6:
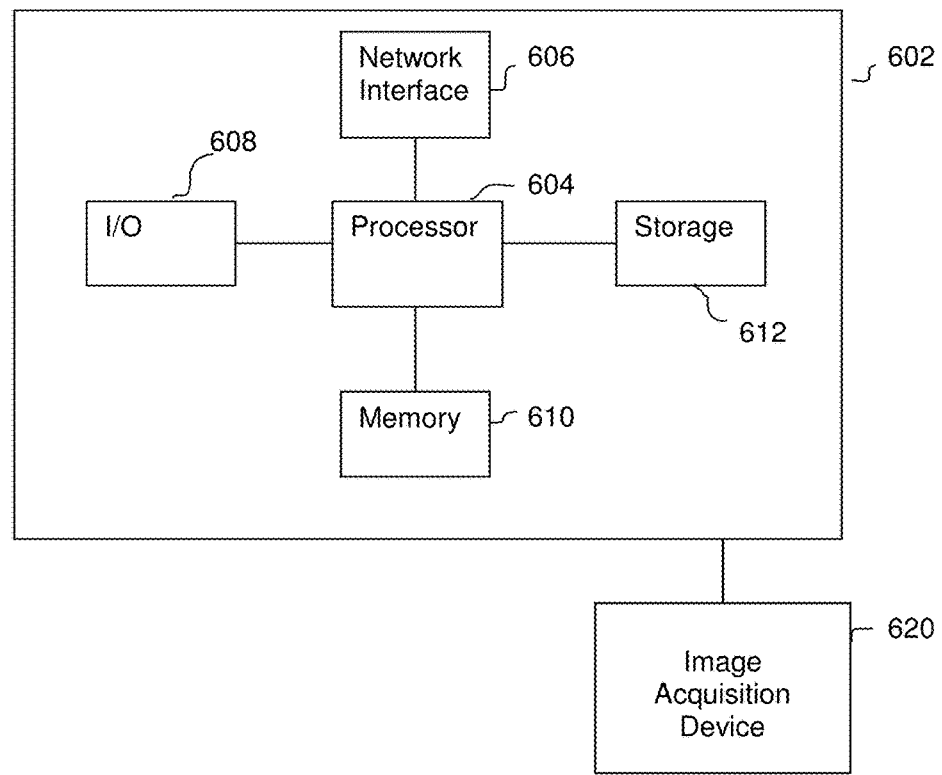
FIG. 6 is a high-level block diagram of a computer capable of implementing the present invention.

The above-described methods for patient-specific simulation of atrial electrophysiological can be implemented on a computer using well-known computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the method of FIG. 1 may be defined by the computer program instructions stored in the memory 610 and/or storage 612 and controlled by the processor 604 executing the computer program instructions. The processor 602 may include one or more central processing unit (CPU) and/or one or more graphics processing unit (GPU) or general purpose graphics processing unit (GPGPU). An image acquisition device 620, such as an MRI scanning device, CT scanning device, C-arm image acquisition device, Ultrasound device, etc., can be connected to the computer 602 to input image data to the computer 602. It is possible to implement the image acquisition device 620 and the computer 602 as one device. It is also possible that the image acquisition device 620 and the computer 602 communicate wirelessly through a network. In a possible embodiment, the computer 602 may be located remotely with respect to the image acquisition device 620 and may perform the method steps as part of a server or cloud based service. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). Such input/output devices 608 may be used in conjunction with a set of computer programs as an annotation tool to annotate volumes received from the image acquisition device 620. One skilled in the art will recognize that an implementation of an actual computer could contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for simulating patient-specific atrial electrophysiology, comprising:
   generating a patient-specific anatomical atria model from medical image data of a patient;
   generating a patient-specific atria electrophysiology model based on the patient-specific anatomical atria model by personalizing electrical conductivity values using electrophysiology measurements of the patient;
   performing one or more virtual electrophysiological therapies by performing atrial electrophysiology simulations using the patient-specific atria electrophysiology model; and
   displaying atrial electrophysiology simulation results resulting from the one or more virtual electrophysiological therapies.

2. The method of claim 1, wherein generating a patient-specific anatomical atria model from medical image data of a patient comprises:
   segmenting a plurality of atria parts in the medical image data using a multi-part atria model; and
   generating a consolidated atria mesh from the segmented plurality of atria parts.

3. The method of claim 2, wherein generating a patient-specific anatomical atria model from medical image data of a patient further comprises:
   tagging a plurality of atrial anatomical structures on the atria mesh.

4. The method of claim 3, wherein the plurality of atrial anatomical structures includes an SA node, Bachmann's bundle, *crista* terminalis, and pectinate muscles.

5. The method of claim 2, wherein generating a patient-specific anatomical atria model from medical image data of a patient further comprises:
   performing mesh thickening on the atria mesh using level-set thresholding from the medical image data.

6. The method of claim 2, wherein generating a patient-specific anatomical atria model from medical image data of a patient further comprises:
   extracting regional atrial wall thickness from the medical image data.

7. The method of claim 2, wherein generating a patient-specific anatomical atria model from medical image data of a patient further comprises:
   segmenting tissue fibrosis in the medical image data; and
   mapping the segmented tissue fibrosis to the atria mesh.

8. The method of claim 1, wherein the patient-specific anatomical atria model is tagged with a plurality of anatomical structures and the patient-specific atria electrophysiology model is a multi-cell electrophysiology model with different cellular models for the plurality of anatomical structures.

9. The method of claim 8, wherein generating a patient-specific atria electrophysiology model based on the patient-specific anatomical atria model by personalizing electrical conductivity values using electrophysiology measurements of the patient comprises:
assigning the electrical conductivity values and multi-cell model parameter values for a plurality of nodes of a computational domain representing the patient-specific anatomical atria model using a rule-based approach based on a clinical report specifying a healthy or disease state of atrial tissue at the plurality of nodes.

10. The method of claim 8, wherein generating a patient-specific atria electrophysiology model based on the patient-specific anatomical atria model by personalizing electrical conductivity values using electrophysiology measurements of the patient comprises:
estimating the personalized electrical conductivity values and multi-cell model parameter values for a plurality of nodes of a computational domain representing the patient-specific anatomical atria model based on the electrophysiology measurements of the patient.

11. The method of claim 10, wherein the electrophysiology measurements of the patient include at least one of body surface potential measurements or invasive electrophysiology maps.

12. The method of claim 10, wherein estimating the personalized electrical conductivity values and multi-cell model parameter values for a plurality of nodes of a computational domain representing the patient-specific anatomical atria model based on the electrophysiology measurements of the patient comprises:
estimating the personalized electrical conductivity values and multi-cell model parameter values for the plurality of nodes of the computational domain to minimize a point-wise difference between simulated activation times calculated using the patient-specific atria electrophysiology model and observed activation times in the electrophysiology measurements of the patient over the plurality of nodes of the computational domain.

13. The method of claim 10, wherein estimating the personalized electrical conductivity values and multi-cell model parameter values for a plurality of nodes of a computational domain representing the patient-specific anatomical atria model based on the electrophysiology measurements of the patient comprises:
calculating the personalized electrical conductivity values and multi-cell model parameter values for the plurality of nodes of the computational domain based on the electrophysiology measurements of the patient by applying a regression function trained with a machine learning method on a database of computed electrophysiology parameters.

14. The method of claim 1, wherein performing one or more virtual electrophysiological therapies by performing atrial electrophysiology simulations using the patient-specific atria electrophysiology model comprises:
performing one or more virtual ablations by performing atrial electrophysiology simulations using the patient-specific atria electrophysiology model.

15. The method of claim 14, wherein performing one or more virtual ablations by performing atrial electrophysiology simulations using the patient-specific atria electrophysiology model comprises:
adjusting the patient-specific atria electrophysiology model based on an ablation location and ablation protocol for each of the one or more virtual ablations; and
simulating action potential propagation in the atria using the adjusted patient-specific atria electrophysiology model for each of the one or more virtual ablations.

16. The method of claim 15, further comprising:
displaying a map showing one or more target ablation locations based on the one or more virtual ablations.

17. The method of claim 15, wherein displaying atrial electrophysiology simulation results resulting from the one or more virtual electrophysiological therapies comprises:
displaying a map showing activation times of the simulated action potential propagation in the atria in the one or more virtual ablations.

18. The method of claim 1, wherein performing one or more virtual electrophysiological therapies by performing atrial electrophysiology simulations using the patient-specific atria electrophysiology model comprises:
adjusting the patient-specific atria electrophysiology model to simulate a physical effect of a drug treatment; and
simulating action potential propagation in the atria using the adjusted patient-specific atria electrophysiology model.

19. The method of claim 18, wherein the patient-specific atria electrophysiology model is a multi-cell electrophysiology model with different cellular models corresponding to different ones of a plurality of ion channels, and adjusting the patient-specific atria electrophysiology model to simulate a physical effect of a drug treatment comprises:
modifying one or more cell model parameters for a cell model corresponding to a specific one or more of the ion channels targeted by the drug treatment.

20. An apparatus for simulating patient-specific atrial electrophysiology, comprising:
a processor; and
a memory storing computer program instructions which when executed by the processor cause the processor to perform operations comprising:
generating a patient-specific anatomical atria model from medical image data of a patient;
generating a patient-specific atria electrophysiology model based on the patient-specific anatomical atria model by personalizing electrical conductivity values using electrophysiology measurements of the patient;
performing one or more virtual electrophysiological therapies by performing atrial electrophysiology simulations using the patient-specific atria electrophysiology model; and
displaying atrial electrophysiology simulation results resulting from the one or more virtual electrophysiological therapies.

21. The apparatus of claim 20, wherein the means for generating a patient-specific anatomical atria model from medical image data of a patient comprises:
means for segmenting a plurality of atria parts in the medical image data using a multi-part atria model; and
means for generating a consolidated atria mesh from the segmented plurality of atria parts.

22. The apparatus of claim 21, wherein the means for generating a patient-specific anatomical atria model from medical image data of a patient further comprises:
means for segmenting tissue fibrosis in the medical image data; and
means for mapping the segmented tissue fibrosis to the atria mesh.

23. The apparatus of claim 20, wherein the patient-specific anatomical atria model is tagged with a plurality of anatomical structures and the patient-specific atria electrophysiology model is a multi-cell electrophysiology model with different cellular models for the plurality of anatomical structures.

24. The apparatus of claim 23, wherein generating a patient-specific atria electrophysiology model based on the patient-specific anatomical atria model by personalizing electrical conductivity values using electrophysiology measurements of the patient comprises:
estimating the personalized electrical conductivity values and multi-cell model parameter values for a plurality of nodes of a computational domain representing the patient-specific anatomical atria model based on the electrophysiology measurements of the patient.

25. The apparatus of claim 20, wherein the means for performing one or more virtual electrophysiological therapies by performing atrial electrophysiology simulations using the patient-specific atria electrophysiology model comprises:
means for performing one or more virtual ablations by performing atrial electrophysiology simulations using the patient-specific atria electrophysiology model.

26. The apparatus of claim 25, wherein the means for performing one or more virtual ablations by performing atrial electrophysiology simulations using the patient-specific atria electrophysiology model comprises:
means for adjusting the patient-specific atria electrophysiology model based on an ablation location and ablation protocol for each of the one or more virtual ablations; and
means for simulating action potential propagation in the atria using the adjusted patient-specific atria electrophysiology model for each of the one or more virtual ablations.

27. The apparatus of claim 26, further comprising:
means for displaying a map showing one or more target ablation locations based on the one or more virtual ablations.

28. The apparatus of claim 20, wherein the means for performing one or more virtual electrophysiological therapies by performing atrial electrophysiology simulations using the patient-specific atria electrophysiology model comprises:
means for adjusting the patient-specific atria electrophysiology model to simulate a physical effect of a drug treatment; and
means for simulating action potential propagation in the atria using the adjusted patient-specific atria electrophysiology model.

29. The apparatus of claim 28, wherein the patient-specific atria electrophysiology model is a multi-cell electrophysiology model with different cellular models corresponding to different ones of a plurality of ion channels, and the means for adjusting the patient-specific atria electrophysiology model to simulate a physical effect of a drug treatment comprises:

means for modifying one or more cell model parameters for a cell model corresponding to a specific one of the ion channels targeted by the drug treatment.

30. A non-transitory computer readable medium storing computer program instructions for simulating patient-specific atrial electrophysiology, the computer program instructions when executed by a processor cause the processor to perform operations comprising:
generating a patient-specific anatomical atria model from medical image data of a patient;
generating a patient-specific atria electrophysiology model based on the patient-specific anatomical atria model by personalizing electrical conductivity values using electrophysiology measurements of the patient;
performing one or more virtual electrophysiological therapies by performing atrial electrophysiology simulations using the patient-specific atria electrophysiology model; and
displaying atrial electrophysiology simulation results resulting from the one or more virtual electrophysiological therapies.

31. The non-transitory computer readable medium of claim 30, wherein generating a patient-specific anatomical atria model from medical image data of a patient comprises:
segmenting a plurality of atria parts in the medical image data using a multi-part atria model; and
generating a consolidated atria mesh from the segmented plurality of atria parts.

32. The non-transitory computer readable medium of claim 31, wherein generating a patient-specific anatomical atria model from medical image data of a patient further comprises:
tagging a plurality of atrial anatomical structures on the atria mesh.

33. The non-transitory computer readable medium of claim 31, wherein generating a patient-specific anatomical atria model from medical image data of a patient further comprises:
performing mesh thickening on the atria mesh using level-set thresholding from the medical image data.

34. The non-transitory computer readable medium of claim 31, wherein generating a patient-specific anatomical atria model from medical image data of a patient further comprises:
extracting regional atrial wall thickness from the medical image data.

35. The non-transitory computer readable medium of claim 31, wherein generating a patient-specific anatomical atria model from medical image data of a patient further comprises:
segmenting tissue fibrosis in the medical image data; and
mapping the segmented tissue fibrosis to the atria mesh.

36. The non-transitory computer readable medium of claim 30, wherein the patient-specific anatomical atria model is tagged with a plurality of anatomical structures and the patient-specific atria electrophysiology model is a multi-cell electrophysiology model with different cellular models for the plurality of anatomical structures.

37. The non-transitory computer readable medium of claim 36, wherein generating a patient-specific atria electrophysiology model based on the patient-specific anatomical atria model by personalizing electrical conductivity values using electrophysiology measurements of the patient comprises:
estimating the personalized electrical conductivity values and multi-cell model parameter values for a plurality of nodes of a computational domain representing the patient-specific anatomical atria model based on the electrophysiology measurements of the patient.

38. The non-transitory computer readable medium of claim 37, wherein estimating the personalized electrical conductivity values and multi-cell model parameter values for a plurality of nodes of a computational domain representing the patient-specific anatomical atria model based on the electrophysiology measurements of the patient comprises:
   estimating the personalized electrical conductivity values and multi-cell model parameter values for the plurality of nodes of the computational domain to minimize a point-wise difference between simulated activation times calculated using the patient-specific atria electrophysiology model and observed activation times in the electrophysiology measurements of the patient over the plurality of nodes of the computational domain.

39. The non-transitory computer readable medium of claim 37, wherein estimating the personalized electrical conductivity values and multi-cell model parameter values for a plurality of nodes of a computational domain representing the patient-specific anatomical atria model based on the electrophysiology measurements of the patient comprises:
   calculating the personalized electrical conductivity values and multi-cell model parameter values for the plurality of nodes of the computational domain based on the electrophysiology measurements of the patient using a machine learning based trained regression function.

40. The non-transitory computer readable medium of claim 30, wherein performing one or more virtual electrophysiological therapies by performing atrial electrophysiology simulations using the patient-specific atria electrophysiology model comprises:
   performing one or more virtual ablations by performing atrial electrophysiology simulations using the patient-specific atria electrophysiology model.

41. The non-transitory computer readable medium of claim 40, wherein performing one or more virtual ablations by performing atrial electrophysiology simulations using the patient-specific atria electrophysiology model comprises:
   adjusting the patient-specific atria electrophysiology model based on an ablation location and ablation protocol for each of the one or more virtual ablations; and
   simulating action potential propagation in the atria using the adjusted patient-specific atria electrophysiology model for each of the one or more virtual ablations.

42. The non-transitory computer readable medium of claim 41, wherein the operations further comprise:
   displaying a map showing one or more target ablation locations based on the one or more virtual ablations.

43. The non-transitory computer readable medium of claim 30, wherein performing one or more virtual electrophysiological therapies by performing atrial electrophysiology simulations using the patient-specific atria electrophysiology model comprises:
   adjusting the patient-specific atria electrophysiology model to simulate a physical effect of a drug treatment; and
   simulating action potential propagation in the atria using the adjusted patient-specific atria electrophysiology model.

44. The non-transitory computer readable medium of claim 43, wherein the patient-specific atria electrophysiology model is a multi-cell electrophysiology model with different cellular models corresponding to different ones of a plurality of ion channels, and adjusting the patient-specific atria electrophysiology model to simulate a physical effect of a drug treatment comprises:
   modifying one or more cell model parameters for a cell model corresponding to a specific one of the ion channels targeted by the drug treatment.

* * * * *